US009215872B2

(12) United States Patent
Ebbinghaus et al.

(10) Patent No.: US 9,215,872 B2
(45) Date of Patent: Dec. 22, 2015

(54) USE OF SUCCINATE DEHYDROGENASE (SDH) INHIBITORS IN THE TREATMENT OF PLANT SPECIES FROM THE FAMILY OF THE TRUE GRASSES

(75) Inventors: Dirk Ebbinghaus, Wuppertal (DE); Ulrich Krieg, Leverkusen (DE); Carlos Andres Berdugo Agudelo, Bonn (DE); Erich-Christian Oerke, Alfter (DE); Heinz-Wilhelm Dehne, Bonn (DE); Ulrike Steiner-Stenzel, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 913 days.

(21) Appl. No.: 12/929,640

(22) Filed: Feb. 4, 2011

(65) Prior Publication Data

US 2011/0196000 A1    Aug. 11, 2011

Related U.S. Application Data

(60) Provisional application No. 61/303,425, filed on Feb. 11, 2010.

(30) Foreign Application Priority Data

Feb. 5, 2010    (EP) .................................... 10152790

(51) Int. Cl.
| A01N 43/40 | (2006.01) |
| A61K 31/44 | (2006.01) |
| A01N 43/56 | (2006.01) |
| A01N 43/30 | (2006.01) |
| A01N 43/653 | (2006.01) |
| A01N 43/88 | (2006.01) |
| A01N 61/00 | (2006.01) |

(52) U.S. Cl.
CPC ............... *A01N 43/56* (2013.01); *A01N 43/30* (2013.01); *A01N 43/40* (2013.01); *A01N 43/653* (2013.01); *A01N 43/88* (2013.01); *A01N 61/00* (2013.01)

(58) Field of Classification Search
USPC .................................................. 514/355, 357
See application file for complete search history.

(56) References Cited

U.S. PATENT DOCUMENTS

| 5,789,566 | A | 8/1998 | Bonhomme et al. |
| 5,866,782 | A | 2/1999 | Iwabuchi et al. |
| 6,229,072 | B1 | 5/2001 | Burns et al. |
| 2004/0204470 | A1 | 10/2004 | Elbe et al. |
| 2005/0234110 | A1 | 10/2005 | Mansfield et al. |
| 2006/0116414 | A1 | 6/2006 | Dunkel et al. |
| 2006/0211574 | A1 | 9/2006 | Buberl et al. |
| 2007/0060579 | A1 | 3/2007 | Wachendorff-Neumann et al. |
| 2008/0015244 | A1 | 1/2008 | Dunkel et al. |
| 2008/0153707 | A1 | 6/2008 | Gewehr et al. |
| 2008/0269263 | A1 | 10/2008 | Dahmen et al. |
| 2009/0011937 | A1 | 1/2009 | Vantieghem et al. |
| 2009/0105311 | A1 | 4/2009 | Dunkel et al. |
| 2009/0133162 | A1 | 5/2009 | Fernandes et al. |
| 2010/0029698 | A1 | 2/2010 | Voeste et al. |
| 2010/0050296 | A1 | 2/2010 | Puzio et al. |
| 2010/0093715 | A1* | 4/2010 | Voeste et al. ............... 514/229.2 |
| 2010/0170011 | A1 | 7/2010 | Lee et al. |
| 2010/0184816 | A1 | 7/2010 | Hauser-Hahn |
| 2010/0324101 | A1 | 12/2010 | Ebbinghaus et al. |
| 2010/0331181 | A1 | 12/2010 | Groeger et al. |
| 2011/0003869 | A1 | 1/2011 | Wetcholowsky et al. |
| 2011/0065580 | A1 | 3/2011 | Rieck et al. |

FOREIGN PATENT DOCUMENTS

| CA | 2541646 | * | 9/2004 |
| EP | 0 737 682 B1 | | 1/2002 |
| EP | 2 039 771 A2 | | 3/2009 |
| EP | 2071953 | * | 6/2009 |
| WO | WO 91/02069 A1 | | 2/1991 |
| WO | WO 95/09910 A1 | | 4/1995 |
| WO | WO 98/27806 A1 | | 7/1998 |
| WO | WO 01/64928 A2 | | 9/2001 |
| WO | WO 03/074491 A1 | | 9/2003 |
| WO | WO 2004/035589 A1 | | 4/2004 |
| WO | WO 2005/002324 A2 | | 1/2005 |
| WO | WO 2005/018324 A2 | | 3/2005 |
| WO | WO 2006/015865 A1 | | 2/2006 |
| WO | WO 2006/015866 A1 | | 2/2006 |
| WO | WO 2006/021972 A1 | | 3/2006 |
| WO | WO 2006/089876 A1 | | 8/2006 |
| WO | WO 2007/090788 A2 | | 8/2007 |
| WO | WO 2009/098218 A2 | | 8/2009 |
| WO | WO 2009/098223 A2 | | 8/2009 |
| WO | WO 2010/000612 A1 | | 1/2010 |

OTHER PUBLICATIONS

Rheinheimer, J., "Fungicides Acting on Oxidative Phosphorylation: Succinate Dehydrogenase Inhibitors," in *Modern Crop Protection Compounds*, Krämer, W. and Schirmer, U. (eds.), vol. 2, Sect. 13.3, pp. 496-505, Wiley-VCH Verlag GmbH, Germany (2007).
Co-pending U.S. Appl. No. 13/087,144, filed Apr. 14, 2011, inventor Dirk Ebbinghaus, United States Patent and Trademark Office, Alexandria, VA, United States (Unpublished).
Office Action mailed Apr. 24, 2012, in U.S. Appl. No. 12/786,663, inventors Ebbinghaus et al., filed May 25, 2010.
Final Office Action mailed Oct. 26, 2012, in U.S. Appl. No. 12/786,663, inventors Ebbinghaus et al., filed May 25, 2010.

* cited by examiner

*Primary Examiner* — Marcos Sznaidman
(74) *Attorney, Agent, or Firm* — Sterne, Kessler, Goldstein & Fox P.L.L.C.

(57) ABSTRACT

The use is described of at least one succinate dehydrogenase (SDH) inhibitor for increasing the biomass of the flag leaf, of leaf F-1 and/or of leaf F-2 of the plant of plant species from the family of the true grasses (Poaceae).

13 Claims, No Drawings

USE OF SUCCINATE DEHYDROGENASE (SDH) INHIBITORS IN THE TREATMENT OF PLANT SPECIES FROM THE FAMILY OF THE TRUE GRASSES

The present invention relates to the specific use of succinate dehydrogenase (SDH) inhibitors in the treatment of plant species from the family of the true grasses (Poaceae).

The present invention relates more particularly to the specific use of succinate dehydrogenase (SDH) inhibitors in the treatment of plant species from the family of true grasses (Poaceae) for the purpose of increasing the biomass of the plant. More particularly the present invention relates to the specific use of succinate dehydrogenase (SDH) inhibitors in the treatment of plant species from the family of the true grasses (Poaceae) for the purpose of increasing the biomass of the flag leaf, of leaf F1 and/or of leaf F2 of the plant.

The use of succinate dehydrogenase (SDH) inhibitors for controlling phytopathogenic fungi and microorganisms is known from the prior art:

Thus, for example, WO 03/070705 A1 describes the use of the succinate dehydrogenase (SDH) inhibitor N-(3',4'-dichloro-5-fluoro-1,1'-biphenyl-2-yl)-3-(difluoromethyl)-1-methyl-1H-pyrazole-4-carboxamide (referred to below by the common name bixafen) for controlling unwanted microorganisms and phytopathogenic fungi.

From WO 2009/106633 A1 it is known that phytopathogenic fungi and microorganisms can be treated effectively with mixtures of bixafen and epoxiconazole or metconazole. These mixtures, in accordance with the teaching of WO 2009/106633 A1, are applied directly to the seed or to the soil of the plants.

WO 2006/131221 A1 teaches the use of bixafen for controlling pathogenic fungi, more particularly soyabean rust; *Phakopsora* species, such as, for example, *Phakopsora sojae*, *Phakopsora pachyrhizi* and *Phakopsora vignae*; *Uredo sojae* and *Uromyces sojae*; but also against other kinds of rust, such as, for example, the coffee rust *Hemileia vastatrix*.

Not apparent from these publications is any reference to the effect of succinate dehydrogenase (SDH) inhibitors in increasing the yield.

WO 01/64928 A2 describes a method for increasing the biomass of monocotyledonous plants, such as rice, wheat, barley, oats or millet, and dicotyledonous plants, such as peas, alfalfa, chickpeas, chicory, kale or lentils, and for increasing the yield of these plants in respect of seed production and plant biomass. In the case of wheat, the harvest index was employed for the purpose of describing the effect. The functional activity of the plants was described on the basis of the increase in total number of kernels, the increase in the individual kernel weight, the increase in the total kernel weight per plant and of the above-ground biomass, the increase of the harvest index, and the improvement in heat stability. The method for increasing the plant biomass in WO 01/64928 A2 is based on transgenic manipulation of the plants and not—as set out later on in the present case—on the use of specific active ingredients. WO 01/64928 A2 likewise contains no indications of any combined treatment of transgenic plants and a fungicidally active component.

Similar methods, encompassing a genetic method for producing transgenic plants for the purpose of increasing the biomass, are known from WO 2003/096797 A2, WO 2006/013010 A2, or WO 2008/142163 A2.

WO 2009/098218 A2 discloses a method for improving plant health by treatment with various SDH inhibitors and also combinations of SDH inhibitors and other pesticides. The term plant health, according to the definition in WO 2009/098218, encompasses the yield and the vitality of the plants and also the tolerance towards abiotic stress factors. No influence of the treatment on flag leaf growth is shown.

EP 2 039 771 A2 discloses a method for improving the production potential of transgenic plants, especially maize, through treatment with bixafen. One of the measures mentioned for improving the production potential of the plants is the resistance of the plants towards abiotic stress. Biological data demonstrating this effect are absent from EP 2 039 771 A2.

WO 2005/018324 A2 discloses a method for boosting plant growth by means of amide compounds, such as boscalid, for example. Bixafen is not disclosed. In that application as well no effect of the treatment on flag leaf growth is shown.

It has now been found that it is particularly advantageous to employ succinate dehydrogenase (SDH) inhibitors for the purpose of increasing the yield in plant species from the family of the true grasses (Poaceae). Having proven effective in particular is the application of succinate dehydrogenase (SDH) inhibitors in the development stages BBCH 12 to 70, preferably in the development stages BBCH 17 to 70, more preferably in the development stages BBCH 20 to 65, more preferably in the development stages BBCH 29 to 60, and very preferably in the development stages BBCH 33 to 55. As well as increasing the yield, the succinate dehydrogenase (SDH) inhibitors proved at the same time to be effective in particular in improving the physiological condition of the plants from the family of the true grasses (Poaceae) and in the control of specific phytopathogens, more particularly *Puccinia triticina*, *Blumeria graminis* and *Septoria tritici*.

For the purposes of the present invention, a plant to be treated is more particularly a plant from development stage BBCH 12 onwards, preferably from development stage BBCH 20, more preferably from development stage BBCH 29, and even more preferably from development stage BBCH 33. The definitions of the BBCH stages are given in the BBCH monograph of the Biologische Bundesanstalt für Land- and Forstwirtschaft, 2nd edition, 2001.

The present invention accordingly provides a method for increasing the yield of plants from the family of the true grasses (Poaceae). The improvement in the physiological condition of the plant, achieved in general at the same time, relates in general to increased physiological activity on the part of the plant, as manifested, for example, in a longer duration of green coloration of the plant. Effects of the inventive use on the physiology of the plant are described in more detail later on below.

The present invention relates in a first aspect to the use of at least one succinate dehydrogenase (SDH) inhibitor on plant species from the family of the true grasses (Poaceae) for the purpose of increasing the yield through increasing the biomass of the flag leaf, of leaf F-1 and/or of leaf F-2 of the plant.

The boost to yield that is achieved through the application of succinate dehydrogenase (SDH) inhibitors is preferably not attributable to the known fungicidal activity of the succinate dehydrogenase (SDH) inhibitors against phytopathogens; in particular, with the approach taken by the invention, a boost to yield can be achieved even in the absence of phytopathogens.

In the context of the present invention it has emerged that, as already mentioned, the at least one succinate dehydrogenase (SDH) inhibitor is applied preferably at a point in time which corresponds to one of the development stages BBCH 12 to 70, preferably one of the development stages BBCH 20 to 65, more preferably one of the development stages BBCH 29 to 60, very preferably one of the development stages BBCH 33 to 55. If application of the succinate dehydrogenase (SDH) inhibitor takes place at this point in time in the development of the plant, the boost to yield is particularly marked.

It is additionally preferred, furthermore, if the at least one succinate dehydrogenase (SDH) inhibitor is applied at not less than two points in time during the development of the plant species. The second treatment takes place preferably at a point in time at which, on the plant to be treated, at least leaf F-2, more preferably at least leaf F-2 and leaf F-1, more preferably still the flag leaf, leaf F-1 and leaf F-2, have developed. In this case the application of the succinate dehydrogenase (SDH) inhibitor takes place more particularly by means of spray application to the aforementioned leaves, in other words the flag leaf, the leaf F-1 and/or the leaf F-2. Overall, in this way, greater growth of these leaves is achieved. The first application preferably takes place at a point in time of development stage BBCH 17 to 42 of the plant species, and the second application at a point in time of development stage BBCH 43 to 70 of the plant species. Corresponding boosts in growth can be achieved, however, not only with this two-stage application of the succinate dehydrogenase (SDH) inhibitors, but also if there is only a first application at the development stages identified above.

Through the present invention, therefore, it is possible more particularly to improve the size and/or area of the flag leaf, of leaf F-1 and/or of leaf F-2. This may be ascertained from the length and the width of the leaves in question.

In a further aspect of the present invention, therefore, the present invention relates to the use of at least one succinate dehydrogenase (SDH) inhibitor on plant species from the family of the true grasses (Poaceae) for increasing the size and/or area of at least one plant leaf, selected from the group consisting of the flag leaf, leaf F-1 and leaf F-2.

Since, in the inventive use of at least one succinate dehydrogenase (SDH) inhibitor, the size and/or area of the aforementioned leaves is increased, there is generally, in the context of the present invention, also an increase in the biomass of the plant. In a further aspect, therefore, the present invention relates to the use of at least one succinate dehydrogenase (SDH) inhibitor for increasing the biomass of plants.

More particularly it is possible through the inventive use of at least one succinate dehydrogenase (SDH) inhibitor to improve the biomass of ears, cereal kernels or ears and cereal kernels, or cereal kernels per ear (number of kernels per ear), of the treated plant.

Furthermore, in accordance with a further aspect, it has been found that the specific inventive application of at least one succinate dehydrogenase (SDH) inhibitor is able not only to increase the biomass and/or the yield of the treated plant but also to improve the physiological condition of the plant overall.

Improved plant physiology is manifested, for example, in a longer duration of green leaf coloration of the plant. Accordingly, in the context of the present invention, it has been found that the specific inventive application of the at least one succinate dehydrogenase (SDH) inhibitor makes it possible to prolong the green leaf area duration. This delays the maturation (senescence) of the plant, which to the farmer denotes an advantage on the basis of greater flexibility in the harvesting time. At the same time, the yellowing of such plants is likewise delayed.

Therefore, the present invention also relates to the use of at least one succinate dehydrogenase (SDH) inhibitor for application to plant species from the family of the true grasses (Poaceae) in order to prolong the green leaf area duration.

The present invention also relates, furthermore, to the use of at least one succinate dehydrogenase (SDH) inhibitor for application to plant species from the family of the true grasses (Poaceae) in order to achieve delayed maturation (senescence) of the plant.

In particular it is possible by means of the application of the inventively provided succinate dehydrogenase (SDH) inhibitor for the development of the ears of cereal plants to be delayed or standardized (this being marked by a later time of heading and an earlier end of heading). Accordingly, the investigations carried out show that, by virtue of the inventive application of succinate dehydrogenase (SDH) inhibitors, the appearance of ears can be delayed by up to a week. The advantage of delayed heading (ear emergence), which takes place generally at BBCH macro-stage 5 and begins in BBCH development stage 51, is that this delay produces an increased biomass.

The advantage of more uniform heading is that, with the plants that are under the spotlight in accordance with the invention, infestation with *Fusarium* pathogens occurs frequently during the period of heading, and a more uniform heading, i.e. a shorter time of heading per se, allows targeted control of the *Fusarium* pathogen during this period.

In the context of the present invention it has additionally been found that through the specific inventive application of at least one succinate dehydrogenase (SDH) inhibitor the chlorophyll content produced in the plant is increased. It has additionally been found that through the application of at least one succinate dehydrogenase (SDH) inhibitor the chlorophyll content in the plant is stabilized. A stabilized chlorophyll content in the context of the present invention means that the breakdown of the chlorophyll in the plant is slower, owing to the inventive application, than in an untreated plant.

The present invention, accordingly, also relates to the use of at least one succinate dehydrogenase (SDH) inhibitor for application to plant species from the family of the true grasses (Poaceae) in order to achieve an increased chlorophyll content and/or a stabilized chlorophyll content in the plant.

It has been ascertained, furthermore, that an increased photosynthesis rate may occur in the plants by virtue of the inventive application. The present invention therefore also relates to the use of at least one succinate dehydrogenase (SDH) inhibitor for application to plant species from the family of the true grasses (Poaceae) in order to achieve an increased photosynthesis rate in the plant.

This increased photosynthesis rate of the plant may be accompanied by delayed senescence of the plant.

In the context of the present invention it has been found, furthermore, that through the specific inventive application of at least one succinate dehydrogenase (SDH) inhibitor, finally, it is possible to improve the resistance or tolerance of plants towards abiotic stress factors. Thus in the case of heat stress it is found that plants treated with at least one succinate dehydrogenase (SDH) inhibitor exhibit an improved transpiration rate and hence an improved evaporative cooling.

The term tolerance or resistance towards abiotic stress is understood in the context of the present invention to encompass various kinds of advantages for plants that are not directly associated with the known fungicidal activity of succinate dehydrogenase (SDH) inhibitors. Such advantageous properties are manifested, for example, in the improved plant characteristics identified as follows: improved root growth in terms of surface area and depth, increased tillering or stolonization, stronger and more productive tillers and stolons, improvement in shoot growth, increased standing power, increased shoot base diameters, increased leaf area, higher yields of nutrients and constituents, such as carbohydrates, fats, oil, proteins, vitamins, minerals, essential oils, dyes, fibres, for example, better fibre quality, earlier flowering, increased number of flowers, reduced level of toxic products such as mycotoxins, reduced level of residues or disadvantageous constituents of any kind, or better digestibility, improved stability of the harvested crop in storage, improved tolerance to inclement temperatures, improved tolerance to drought and dryness, and also to lack of oxygen as a result of waterlogging, improved tolerance towards increased salt levels in soils and water, increased tolerance towards ozone stress, improved tolerance to herbicides and other plant treatment products, improved water uptake and photosynthesis rate, advantageous plant properties, such as, for example, altered maturation, more uniform maturation, greater attraction for beneficial organisms, improved pollination or other advantages which are well known to a person skilled in the art.

The above-described effects of the succinate dehydrogenase (SDH) inhibitors may occur individually or else simultaneously and can be demonstrated typically with terms that have general validity. Examples of such terms include the designations set out as follows: phytotonic effect, resistance to stress factors, less plant stress, plant health, healthy plants, plant fitness, plant wellness, plant concept, vigour effect, stress shield, protective shield, crop health, crop health properties, crop health products, crop health management, crop health therapy, plant health, plant health properties, plant health products, plant health management, plant health therapy, greening effect, re-greening effect, freshness, or other terms which are well known to a person skilled in the art.

Furthermore, the inventively envisaged application of succinate dehydrogenase (SDH) inhibitors is accompanied by successful control of relevant pathogens. This relates to the known application of bixafen for the control of fungicides, but through the specific application of bixafen to the flag leaf, the leaves F-1 and/or F-2, particularly effective control of the pathogens is possible.

Pathogens to be controlled may be selected, in the context of the present invention, from the group consisting of *Ascochyta tritici, Blumeria graminis, Cladosporium herbarum, Cochliobolus sativus, Epicoccum* spp., *Erysiphe graminis, Fusarium graminearum, Fusarium culmorum, Gaeumannomyces graminis, Leptosphaeria nodorum, Microdochium nivale, Pseudocercospora herpotrichoides, Pseudocercosporella herpotrichoides, Puccinia striiformis, Puccinia triticina, Puccinia hordei, Puccinia recondite, Pyrenophora graminea, Pyrenophora teres, Pyrenophora tritici repentis, Ramularia collo-cygni, Rhizoctonia solani, Rhizoctonia cerealis, Rhynchosporium secalis, Septoria nodorum, Septoria tritici, Stagonospora nodorum, Tilletia caries, Typhula incarnate,Uromyces appendiculatus, Ustilago avenae* and *Ustilago nuda*.

The present invention is suitable more particularly for the simultaneous control of pathogens selected from the group consisting of *Puccinia triticina, Blumeria graminis* and *Septoria tritici*.

An assembly of inventive succinate dehydrogenase (SDH) inhibitors is found at www.FRAC.info (Mode of Action Poster, subgroup C2: inhibition of complex II: succinate dehydrogenase, # 7 SDHI Succinate DeHydrogenase Inhibitors).

Particularly preferred succinate dehydrogenase (SDH) inhibitors of the invention may be selected from the group consisting of the following compounds:
(1) Fluopyram, with the chemical name N-{[3-chloro-5-(trifluoromethyl)-2-pyridinyl]ethyl}-2,6-dichlorobenzamide, which is a fungicide from the chemical class of the pyridylethylbenzamides. Fluopyram and its preparation process starting from known and commercially available components are described in publication EP 1 389 614 A.
(2) Penflufen, with the chemical name N-[2-(1,3-dimethylbutyl)phenyl]-5-fluoro-1,3-dimethyl-1H-pyrazole-4-carboxamide. Penflufen and its preparation process starting from known and commercially available components are described in publication WO 2003/010149 A.
(3) Bixafen, with the chemical name N-(3',4'-dichloro-5-fluoro-1,1'-biphenyl-2-yl)-3-(difluoromethyl)-1-methyl-1H-pyrazole-4-carboxamide. Bixafen and its preparation process starting from known and commercially available components are described in publication WO 2003/070705 A.
(4) Sedaxane, which is a mixture of two cis-isomers 2'-[(1RS, 2RS)-1,1'-bicycloprop-2-yl]-3-(difluoromethyl)-1-methylpyrazole-4-carboxanilide and two trans-isomers 2'-[(1RS,2SR)-1,1'-bicycloprop-2-yl]-3-(difluoromethyl)-1-methylpyrazole-4-carboxanilide. Sedaxane and its preparation process starting from known and commercially available components are described in publications WO 2003/074491 A, WO 2006/015865 A and WO 2006/015866 A.
(5) Isopyrazam, which is a mixture of 2 syn-isomers 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl] pyrazole-4-carboxamide. Isopyrazam and its preparation process starting from known and commercially available components are described in publication WO 2004/035589 A.
(6) Penthiopyrad, with the chemical name (RS)-N-[2-(1,3-dimethylbutyl)-3-thienyl]-1-methyl-3-(trifluoromethyl) pyrazole-4-carboxamide. Penthiopyrad and its preparation process starting from known and commercially available components are described in publication EP 0 737 682 A.
(7) Boscalid, with the chemical name 2-chloro-N-(4'-chlorobiphenyl-2-yl)nicotinamide. Boscalid and its preparation process starting from known and commercially available components are described in publication DE 195 31 813 A.
(8) Fluxapyraxad, with the chemical name 3-(difluoromethyl)-1-methyl-N-(3',4',5'-trifluorobiphenyl-2-yl)-1H-pyrazole-4-carboxamide. Fluxapyraxad and its preparation process starting from known and commercially available components are described in publication WO 2006/087343 A.
(9) N-[1-(2,4-Dichlorophenyl)-1-methoxypropan-2-yl]-3-(difluoromethyl)-1-methyl-1H-pyrazol-4-carboxamide, whose preparation process starting from known and commercially available components is described in publication WO 2010/000612 A.

In the context of the present invention it is particularly preferred if bixafen, with the chemical name N-(3',4'-dichloro-5-fluoro-1,1'-biphenyl-2-yl)-3-(difluoromethyl)-1-methyl-1H-pyrazole-4-carboxamide, is used as succinate dehydrogenase (SDH) inhibitor.

It is further preferred if bixafen is used in combination with at least one further active ingredient. The further active ingredient is preferably selected from the group consisting of spiroxamine, fluoxastrobin and prothioconazole. Particularly preferred is a combination of bixafen and prothioconazole.

The inventively envisaged use of succinate dehydrogenase (SDH) inhibitors takes place preferably with a dose of between 0.01 and 3 kg/ha, more preferably between 0.01 and 1.5 kg/ha, and with particular preference between 0.1 and 0.5 kg/ha.

Particularly suitable target crops for the purposes of the present invention are from the family of the true grasses: wheat, rye, barley, oats, millet, maize, rice, triticale, bamboo and sugarcane.

The present invention is suitable, furthermore, for the treatment of winter cereal and spring cereal.

Particular preference is given in accordance with the invention to treating plants of the respective plant varieties which are available commercially or are in use. By plant varieties are meant plants having new properties (traits) which have been cultivated by conventional breeding, by mutagenesis or using recombinant DNA techniques. Accordingly, crop plants may be plants obtainable by conventional breeding and optimization methods or by biotechnological and recombinant methods, or by combinations of these methods, including the transgenic plants and including the plant varieties which may or may not be amenable to protection by varietal property rights (plant breeders' rights).

In the context of the present invention, genetically modified organisms (GMOs) may also be treated. Genetically modified plants (or transgenic plants) are plants in which a heterologous gene has been stably integrated into the genome. The term "heterologous gene" denotes essentially a gene which is provided or assembled outside the plant and which, on introduction into the nuclear genome, the chloroplast genome or the mitochondrial genome, endows the transformed plant with new or improved agronomic or other properties, by expressing a polypeptide or protein of interest or by down-regulating or switching off another gene present in the plant or other genes present in the plant (for example, by means of antisense technology, cosuppression technology or RNAi [RNA Interference] technology). A heterologous gene which is present in the genome is also termed a transgene. A transgene, which is defined by its specific presence in the plant genome, is referred to as a transformation event or transgenic event.

Plants and plant varieties which are treated preferably in accordance with the invention include all plants possessing genetic material that endows these plants with particularly advantageous, useful traits (irrespective of whether this has been achieved through breeding and/or biotechnology).

Plants and plant varieties which may likewise be treated in accordance with the invention are those plants which are resistant to one or more abiotic stress factors. The abiotic stress conditions may include, for example, drought, conditions of cold and of heat, osmotic stress, water logging, increased soil salinity, increased exposure to minerals, ozone conditions, strong light conditions, limited availability of nitrogen nutrients, limited availability of phosphorus nutrients, or shade avoidance.

Plants and plant varieties that may likewise be treated in accordance with the invention are those plants which are characterized by increased yield properties. Increased yield in these plants may derive, for example, from improved plant physiology, improved plant growth and improved plant development, such as water utilisation efficiency, water retention efficiency, improved nitrogen use, enhanced carbon assimilation, improved photosynthesis, increased germination efficiency, and altered maturation. Yield may additionally be affected by an improved architecture (under stress and non-stress conditions), including early flowering, control of flowering for production of hybrid seed, seedling vigour, plant size, internode number and distance, root growth, seed size, fruit size, pod size, number of pods or ears, number of seeds per pod or ear, seed mass, increased seed filling, reduced seed dispersal, reduced pod dehiscence, and lodging resistance. Further yield traits include seed composition such as carbohydrate content, protein content, oil content and oil composition, nutritional value, reduction in anti-nutritional compounds, improved processing properties and improved storage qualities.

Plants that may likewise be treated in accordance with the invention are hybrid plants which already express the characteristics of heterosis, or the hybrid effect, which results generally in higher yield, greater vigour, better health and better resistance towards biotic and abiotic stress factors. Plants of this kind are typically produced by crossing an inbred male-sterile parent line (the female crossing partner) with another inbred male-fertile parent line (the male crossing partner). The hybrid seed is typically harvested from the male-sterile plants and sold to growers. Male-sterile plants may sometimes (as in the case of maize, for example) be produced by detasselling (i.e. mechanical removal of the male reproductive organs or male flowers); it is, however, more usual for the male sterility to derive from genetic determinants in the plant genome. In that case, especially when the desired product it is desired to harvest from the hybrid plants is the seeds, it is typically useful to ensure that the male fertility is fully restored in hybrid plants which contain genetic determinants that are responsible for the male sterility. This can be accomplished by ensuring that the male crossing partners possess corresponding fertility restorer genes, which are capable of restoring male fertility in hybrid plants which contain the genetic determinants that are responsible for the male sterility. Genetic determinants for male sterility may be located in the cytoplasm. Examples of cytoplasmic male sterility (CMS) have been described, for example, for *Brassica* species (WO 1992/005251, WO 1995/009910, WO 1998/27806, WO 2005/002324, WO 2006/021972 and U.S. Pat. No. 6,229,072). Genetic determinants for male sterility may also, however, be located in the nuclear genome. Male-sterile plants can also be obtained by methods of plant biotechnology, such as genetic engineering. One particularly useful means of generating male-sterile plants is described in WO 89/10396, where, for example, a ribonuclease such as a Barnase is expressed selectively in the tapetum cells in the stamens. Fertility can then be restored by expression of a ribonuclease inhibitor such as barstar in the tapetum cells (e.g. WO 1991/002069).

In the context of the present invention, the succinate dehydrogenase (SDH) inhibitor may be used in the form of a formulation.

The active ingredient of the invention may be present in its standard commercial formulations and also in the application forms that are prepared in these formulations, in a mixture with other active ingredients such as insecticides, attractants, sterilants, bactericides, acaricides, nematicides, fungicides, growth regulators, herbicides, safeners, fertilizers or semiochemicals.

In this case the succinate dehydrogenase (SDH) inhibitor for use in accordance with the invention may be used in customary formulations, such as solutions, emulsions, wettable powders, water-based and oil-based suspensions and suspension-emulsion concentrates.

In the context of the present invention it is particularly preferred if the succinate dehydrogenase (SDH) inhibitor envisaged in accordance with the invention is used in the form of a spray formulation.

Corresponding formulations and their constituents are known per se to a person skilled in the art.

The examples which follow describe the invention in detail, but in no way limit the present invention.

EXPERIMENTAL DESCRIPTION

Example 1

In Germany a plot trial was set up with the wheat variety Ritmo in order to investigate the effect of bixafen on the physiology, morphology and abiotic stress tolerance of wheat plants under realistic agricultural conditions.

The products under test were applied to the plants, in the form of sequential spray sequences (BBCH 39 and 59). The spray volume was 400 l of water per hectare. In each trial component, 5 repetitions were carried out.

| Active ingredient(s) | Formulation | Active ingredient content [g a.i./l] | Application rate [l/ha] | Amount applied [g/ha] |
|---|---|---|---|---|
| Bixafen | EC | 125 | 1 | 125 |
| Fluoxastrobin | EC | 100 | 2 | 200 |
| Prothioconazole | EC | 250 | 0.8 | 200 |
| Spiroxamine | EC | 500 | 0.75 | 375 |
| Boscalid | WG | 500 g/kg | 1 kg/ha | 500 g/ha |
| Spiroxamine + Prothioconazole | EC | 300 + 160 | 1.25 | 375 + 200 |
| Bixafen + Prothioconazole | EC | 75 + 150 | 1.25 | 94 + 188 |

Subsequently, non-invasive and invasive methods were applied for capturing the plant development and plant physiology. In addition, parameters relevant to yield were captured. Results of Example 1:

The duration of green coloration of the leaf area was captured by regular visual scoring of the fraction of green leaf area.

The trials show that the succinate dehydrogenase (SDH) inhibitor bixafen has a pronounced effect on the duration of the green leaf area of the wheat plant. The effect of bixafen alone can be increased still further by combination with a fungicide, particularly with the fungicide prothioconazole.

TABLE 1

Influence of fungicide treatments on the green leaf area of the flag leaf (% leaf area)

| Treatment | Days after second fungicide application | | | | | |
|---|---|---|---|---|---|---|
| | 7 | 14 | 21 | 28 | 35 | 42 |
| Untreated | 97.5 | 92.5 | 74.5 | 63.1 | 0 | 0 |
| Bixafen (BIX) | 98.9 | 98.7 | 98.8 | 96.7 | 73.0 | 26.7 |
| Fluoxastrobin | 98.7 | 98.7 | 98.3 | 95.8 | 63.0 | 23.7 |
| Prothioconazole (PTZ) | 98.8 | 98.2 | 98.1 | 94.0 | 58.8 | 13.8 |
| Spiroxamine (SPR) | 98.3 | 97.9 | 92.7 | 82.3 | 48.6 | 5.5 |
| Boscalid | 96.0 | 95.5 | 86.1 | 73.6 | 43.2 | 7.0 |
| BIX + PTZ | 98.8 | 98.8 | 98.7 | 97.8 | 76.5 | 38.0 |
| SPR + PTZ | 98.9 | 98.6 | 98.6 | 95.6 | 54.6 | 12.6 |

TABLE 2

Effect of fungicide treatments on the green leaf area of the second-from-top leaf (F-1; % leaf area)

| Treatment | Days after second fungicide application | | | | | | |
|---|---|---|---|---|---|---|---|
| | 7 | 14 | 21 | 28 | 35 | 42 | 49 |
| Untreated | 94.6 | 87.1 | 57.1 | 41.5 | 0 | 0 | 0 |
| Bixafen (BIX) | 98.4 | 98.3 | 98.5 | 94.8 | 60.0 | 9.2 | 0 |
| Fluoxastrobin | 98.8 | 98.0 | 96.1 | 93.5 | 47.0 | 9.8 | 0 |
| Prothioconazole (PTZ) | 97.8 | 97.8 | 96.8 | 91.2 | 44.3 | 4.2 | 0 |
| Spiroxamine (SPR) | 97.4 | 95.8 | 85.8 | 69.7 | 31.7 | 0 | 0 |
| Boscalid | 94.4 | 91.8 | 74.7 | 60.0 | 25.5 | 0 | 0 |
| BIX + PTZ | 98.6 | 98.5 | 98.4 | 95.8 | 61.0 | 22.7 | 0 |
| SPR + PTZ | 97.6 | 97.4 | 97.3 | 93.4 | 36.3 | 3.7 | 0 |

TABLE 3

Effect of fungicide treatments on the green leaf area of the third-from-top leaf (F-2; % leaf area)

| Treatment | Days after second fungicide application | | | | | |
|---|---|---|---|---|---|---|
| | 7 | 14 | 21 | 28 | 35 | 42 |
| Untreated | 89.6 | 79.5 | 41.7 | 19.7 | 0 | 0 |
| Bixafen (BIX) | 96.4 | 96.3 | 94.5 | 91.8 | 37.5 | 3.4 |
| Fluoxastrobin | 96.3 | 95.5 | 92.1 | 88.5 | 31.5 | 1.9 |
| Prothioconazole (PTZ) | 96.1 | 95.9 | 94.9 | 83.7 | 25.3 | 0 |
| Spiroxamine (SPR) | 94.1 | 93.3 | 78.1 | 51.7 | 15.7 | 0 |
| Boscalid | 90.3 | 85.8 | 61.5 | 41.0 | 4.6 | 0 |
| BIX + PTZ | 96.7 | 96.6 | 96.2 | 94.2 | 43.0 | 9.0 |
| SPR + PTZ | 95.6 | 95.4 | 93.7 | 87.7 | 22.1 | 0 |

The chlorophyll content of treated and untreated plants was determined by the pigment extraction method of Ziegler and Ehle. Factors relevant to yield that were captured were the kernel yield, the thousand-kernel mass, the number of ears/plot, and the straw mass.

It is found that, where at least one succinate dehydrogenase (SDH) inhibitor, for example bixafen, is used alone or else in combination with other active fungicidal ingredients, such as prothioconazole in particular, the chlorophyll content overall is higher and the breakdown of chlorophyll is slower; the chlorophyll in the plant, therefore, is stabilized. This is apparent from a comparison of the chlorophyll content at different stages of development (cf. Table 4) of the plant.

TABLE 4

Effect of fungicide treatments on the chlorophyll content of wheat leaves at development stages BBCH 75 (mature milk) and BBCH 85 (mature dough)

| Treatment | Chlorophyll content [µg g$^{-1}$] | | | | | |
|---|---|---|---|---|---|---|
| | BBCH 75 | | | BBCH 85 | | |
| | F | F-1 | F-2 | F | F-1 | F-2 |
| Untreated | 1328 | 990 | 555 | 121 | 119 | 220 |
| Bixafen (BIX) | 1763 | 1693 | 1243 | 738 | 631 | 404 |
| Fluoxastrobin | 1924 | 1671 | 1126 | 630 | 534 | 415 |
| Prothioconazole (PTZ) | 1740 | 1637 | 1207 | 211 | 163 | 116 |
| Spiroxamine (SPR) | 1471 | 1245 | 707 | 114 | 119 | 147 |
| Boscalid | 1597 | 1505 | 826 | 188 | 160 | 110 |
| BIX + PTZ | 1915 | 1657 | 1180 | 1200 | 716 | 538 |
| SPR + PTZ | 1794 | 1373 | 1012 | 149 | 344 | 189 |

The individual yield components of wheat as well can be improved through the inventive use of at least one succinate dehydrogenase (SDH) inhibitor alone or in combination with a further fungicide (cf. Table 5). This relates to the yield, the thousand-kernel mass, and the number of ears per m$^2$.

TABLE 5

Effect of fungicide treatments on the yield components of wheat

| Treatment | Yield [t ha$^{-1}$] | TKM [g] | Ears/ m$^2$ | Straw [g m$^{-2}$] | Harvest Index |
|---|---|---|---|---|---|
| Untreated | 7.3 | 40.3 | 392 | 467 | 60.3 |
| Bixafen (BIX) | 8.5 | 47.7 | 417 | 590 | 58.5 |
| Fluoxastrobin | 8.2 | 45.8 | 409 | 581 | 58.1 |
| Prothioconazole (PTZ) | 8.1 | 46.3 | 397 | 533 | 59.3 |
| Spiroxamine (SPR) | 7.7 | 44.2 | 409 | 514 | 59.3 |
| Boscalid | 7.8 | 44.6 | 444 | 514 | 58.6 |
| BIX + PTZ | 8.7 | 49.2 | 391 | 600 | 59.6 |
| SPR + PTZ | 8.3 | 45.9 | 395 | 562 | 58.8 |

Example 2

In a glasshouse trial under controlled conditions, the effect of bixafen was investigated on the physiology, morphology and abiotic stress tolerance of infection-free wheat plants of the cultivar Passat.

The wheat plants were grown in 10-litre containers over a period of 4 months. The substrate used was standard earth type ED 73 (Fröndenberg, Germany)+C-Horizont+Sand (4:2:1). The supply of nutrient to the plants took place by feeding with a 0.2% strength Flory 2 liquid fertilizer solution (from Euflor, Munich) once every two weeks. The plants were supplied with water as required. In each component of the trial, 10 repetitions were carried out.

To prevent infestation with powdery mildew, Proquinazid (Talius®) was applied once. The incidence of aphids and spider mites was avoided by treatments with Karate®, Bulldock® and Sumicidin®.

The products under test were applied to the plants, in the form of sequential spray sequences (BBCH 39 and 59). The spray volume was 300 l of water per hectare.

| Active ingredient(s) | Formulation | Active ingredient content [g a.i./l] | Application rate [l/ha] | Amount applied [g/ha] |
|---|---|---|---|---|
| Bixafen | EC | 125 | 1 | 125 |
| Fluoxastrobin | EC | 100 | 2 | 200 |
| Prothioconazole | EC | 250 | 0.8 | 200 |
| Spiroxamine | EC | 500 | 0.75 | 375 |

Subsequently, noninvasive and invasive methods were employed for capturing the plant development and plant physiology. In addition, morphological parameters and parameters relevant to yield were captured.

Results of Example 2:

The duration of the green coloration of the leaf area was captured on the basis of regular visual scoring of the fraction of the green leaf area.

The trials show that the succinate dehydrogenase (SDH) inhibitor bixafen has a pronounced effect on the duration of the green leaf area of the wheat plant.

TABLE 6

Effect of fungicide treatments on the green leaf area of the flag leaf (F; % leaf area)

| | Days after second fungicide application | | | | | | | |
|---|---|---|---|---|---|---|---|---|
| Treatment | 68 | 75 | 82 | 89 | 96 | 103 | 110 | 117 |
| Untreated | 100 | 100 | 100 | 93 | 78 | 53 | 21 | 2 |
| Bixafen | 100 | 100 | 100 | 95 | 88 | 65 | 38 | 15 |
| Fluoxastrobin | 100 | 100 | 100 | 95 | 85 | 60 | 37 | 12 |
| Prothioconazole | 100 | 100 | 100 | 95 | 85 | 62 | 38 | 15 |
| Spiroxamine | 100 | 100 | 100 | 92 | 80 | 55 | 23 | 3 |

TABLE 7

Effect of fungicide treatments on the green leaf area of the second-from-top leaf (F-1; % leaf area)

| | Days after second fungicide application | | | | | | | |
|---|---|---|---|---|---|---|---|---|
| Treatment | 68 | 75 | 82 | 89 | 96 | 103 | 110 | 117 |
| Untreated | 100 | 100 | 92 | 75 | 46 | 22 | 5 | 0 |
| Bixafen (BIX) | 100 | 100 | 95 | 85 | 57 | 33 | 20 | 5 |
| Fluoxastrobin | 100 | 100 | 95 | 84 | 56 | 30 | 18 | 6 |
| Prothioconazole | 100 | 100 | 95 | 83 | 57 | 30 | 19 | 5 |
| Spiroxamine | 100 | 100 | 90 | 77 | 50 | 23 | 6 | 0 |

TABLE 8

Effect of fungicide treatments on the green leaf area of the third-from-top leaf (F-2; % leaf area)

| | Days after second fungicide application | | | | | | | |
|---|---|---|---|---|---|---|---|---|
| Treatment | 68 | 75 | 82 | 89 | 96 | 103 | 110 | 117 |
| Untreated | 100 | 95 | 70 | 40 | 19 | 4 | 0 | 0 |
| Bixafen | 100 | 95 | 80 | 52 | 29 | 15 | 6 | 0 |
| Fluoxastrobin | 100 | 95 | 82 | 54 | 29 | 18 | 7 | 0 |
| Prothioconazole | 100 | 95 | 83 | 53 | 30 | 17 | 8 | 0 |
| Spiroxamine | 100 | 95 | 73 | 45 | 19 | 7 | 0 | 0 |

Additional factors relevant to yield that were captured were the kernel yield, the thousand-kernel mass, the number of ears/container, and the number of kernel/ear (see Table 17).

It is found that the succinate dehydrogenase (SDH) inhibitor bixafen leads to a higher yield, a higher number of kernel/ear, a higher thousand-kernel mass and a lower straw fraction than the other comparison fungicides. Bixafen exhibits a high harvest yield, expressed as the ratio of harvested parts to unusable parts of a plant (called Harvest Index in the language of the art).

TABLE 9

Effect of fungicide treatments on the yield components of wheat

| Treatment | Yield [g/pot] | Ears/ pot | Kernels/ ear | TKM [g] | Straw [g/pot] | Harvest Index [%] |
|---|---|---|---|---|---|---|
| Untreated | 29.6 | 39.0 | 22.7 | 33.5 | 64.6 | 31.4 |
| Bixafen | 37.5 | 40.0 | 25.1 | 37.5 | 88.5 | 29.8 |
| Fluoxastrobin | 30.5 | 41.0 | 21.9 | 34.3 | 74.5 | 29.0 |
| Prothioconazole | 32.1 | 43.1 | 22.2 | 33.5 | 85.4 | 27.3 |
| Spiroxamine | 33.4 | 40.9 | 23.2 | 35.5 | 58.6 | 36.3 |

Morphological parameters measured, additionally, were the length and width, i.e. the size of the flag leaf. This was greatest with the succinate dehydrogenase (SDH) inhibitor bixafen, in comparison to the other comparison fungicides.

TABLE 10

Effect of fungicide treatments on the size of the flag leaf of wheat at BBCH 83-85

| Treatment | Length [cm] | Width [cm] | Area [cm$^2$][1] | Area [rel.] |
|---|---|---|---|---|
| Untreated | 25.1 | 1.3 | 21.86 | 100 |
| Bixafen | 28.1 | 1.7 | 32.01 | 146 |
| Fluoxastrobin | 25.6 | 1.4 | 24.01 | 110 |
| Prothioconazole | 26.7 | 1.3 | 23.26 | 106 |
| Spiroxamine | 26.1 | 1.2 | 20.98 | 96 |

[1] calculated using the formula A = 0.67 × length × width

Additionally evaluated was the effect of fungicide treatments on the time of heading (ear emergence) in wheat. It was found that, using bixafen, the heading is more uniform. Since the plants under the spotlight are frequently infested by *Fusarium* pathogens during the period of heading, a more uniform heading at this point in time allows targeted control of the *Fusarium* pathogen.

TABLE 11

Effect of fungicide treatments on the time of heading of wheat (after 40 days there were still no ears present, after 90 days all of the ears had emerged in all treatments).

| | Days after sowing [d] | | | | | | | | |
|---|---|---|---|---|---|---|---|---|---|
| Treatment | 45 | 50 | 55 | 60 | 65 | 70 | 75 | 80 | 85 |
| Untreated | 17.9 | 45.1 | 48.9 | 54.1 | 64.1 | 76.4 | 83.5 | 96.1 | 100 |
| Bixafen | 1.8 | 15.5 | 42.2 | 57.0 | 78.0 | 88.7 | 93.5 | 96.7 | 98.5 |
| Fluoxastrobin | 11.4 | 33.1 | 43.8 | 49.9 | 61.1 | 76.4 | 87.8 | 93.1 | 97.1 |
| Prothioconazole | 6.9 | 29.0 | 42.6 | 48.2 | 64.1 | 77.9 | 87.1 | 94.9 | 100 |
| Spiroxamine | 10.8 | 34.1 | 46.4 | 57.5 | 75.5 | 83.4 | 91.1 | 99.1 | 100 |

The results shown in Table 12 below demonstrate that plants treated with at least one succinate dehydrogenase (SDH) inhibitor exhibit an improved transpiration rate and hence improved evaporative cooling.

TABLE 12

Effect of fungicide treatments on the temperature of the ears and leaves of wheat (as a measure of the transpiration activity) at the four development stages BBCH 75, 80, 85 and 90.

| | Temperature [° C.] | | | | | | | |
|---|---|---|---|---|---|---|---|---|
| | BBCH 75 | | BBCH 80 | | BBCH 85 | | BBCH 90 | |
| Treatment | ear | leaf | ear | leaf | ear | leaf | ear | lear |
| Untreated | 23.7 | 22.5 | 20.4 | 18.1 | 25.3 | 24.4 | 24.3 | 23.4 |
| Bixafen | 22.3 | 22.1 | 18.2 | 16.4 | 24.5 | 23.3 | 24.1 | 22.3 |
| Fluoxastrobin | 23.1 | 22.3 | 18.9 | 16.5 | 24.8 | 23.4 | 23.9 | 22.7 |
| Prothioconazole | 23.1 | 22.4 | 19.5 | 16.6 | 24.8 | 23.7 | 24.2 | 23.1 |
| Spiroxamine | 23.2 | 22.4 | 20.2 | 16.4 | 25.1 | 23.7 | 24.2 | 23.2 |

As shown in Table 13 below, using a succinate dehydrogenase (SDH) inhibitor it is possible to achieve an increased photosynthesis rate in the plant from the family of the true grasses.

TABLE 13

Effect of fungicide treatments on the gas exchange activity of wheat ears at development stage BBCH 75.

| Treatment | Photosynthesis [CO$_2$ per ear] | Respiration [CO$_2$ per ear] |
|---|---|---|
| Untreated | −0.98 a | 0.80 a |
| Bixafen | −5.94 b | 6.12 c |
| Fluoxastrobin | −2.44 a | 2.96 b |
| Prothioconazole | −1.86 a | 2.12 ab |
| Spiroxamine | −2.36 a | 2.82 b |

Example 3

Effect of Bixafen on Leaf Area

Comparison of Single and Double Treatment with Bixafen

Trial procedure: Wheat plants were treated at different development stages with bixafen once or twice (125 g/ha each time), and a measurement was made of the respective size of the flag leaf and of the leaf F-1 at the time BBCH 75. For the destructive measurement of the leaf area, the leaves were removed from the plant. The non-destructive measurement was carried out on the intact leaf of the plant.

TABLE 14

Effect of bixafen on the size of the flag leaf on wheat at BBCH 75 (non-destructive measurement); n = 15

| Treatment | Length [cm] | Width [cm] | Area [cm$^2$] | Area [rel.] |
|---|---|---|---|---|
| Untreated | 22.84 | 1.69 | 32.42 | 100 |
| Bixafen [BBCH 33] | 25.11 | 1.66 | 35.23 | 109 |
| Bixafen [BBCH 39] | 24.21 | 1.72 | 34.86 | 108 |
| Bixafen [BBCH 59] | 23.78 | 2.02 | 37.91 | 117 |
| Bixafen [BBCH 33 + 39] | 24.49 | 1.76 | 35.37 | 109 |
| Bixafen [BBCH 33 + 59] | 25.83 | 1.73 | 37.41 | 115 |
| Bixafen [BBCH 39 + 59] | 26.83 | 1.77 | 39.44 | 122 |

TABLE 15

Effect of bixafen on the size of the flag leaf of wheat at BBCH 75
(destructive measurement); n = 40

| Treatment | Length [cm] | Width [cm] | Area [cm$^2$] | Area [rel.] |
|---|---|---|---|---|
| Untreated | 25.13 | 1.35 | 27.96 | 100 |
| Bixafen [BBCH 33] | 28.25 | 1.47 | 32.13 | 115 |
| Bixafen [BBCH 39] | 25.81 | 1.40 | 29.04 | 104 |
| Bixafen [BBCH 59] | 26.58 | 1.47 | 32.37 | 116 |
| Bixafen [BBCH 33 + 39] | 24.49 | 1.40 | 29.38 | 105 |
| Bixafen [BBCH 33 + 59] | 27.10 | 1.51 | 31.28 | 112 |
| Bixafen [BBCH 39 + 59] | 26.57 | 1.52 | 32.44 | 116 |

TABLE 16

Effect of bixafen on the size of the leaf F-1 in wheat at BBCH 75
(destructive measurement); n = 40

| Treatment | Length [cm] | Width [cm] | Area [cm$^2$] | Area [rel.] |
|---|---|---|---|---|
| Untreated | 26.91 | 1.26 | 27.55 | 100 |
| Bixafen [BBCH 33] | 30.58 | 1.35 | 32.69 | 119 |
| Bixafen [BBCH 39] | 28.27 | 1.19 | 28.37 | 103 |
| Bixafen [BBCH 59] | 31.10 | 1.26 | 30.55 | 111 |
| Bixafen [BBCH 33 + 39] | 27.68 | 1.27 | 28.42 | 103 |
| Bixafen [BBCH 33 + 59] | 29.77 | 1.30 | 30.07 | 109 |
| Bixafen [BBCH 39 + 59] | 29.38 | 1.20 | 30.28 | 110 |

Example 4

TABLE 17

Effect of bixafen on the number of kernels/ear in wheat (n = 15)

| Treatment | Kernels/ear | Application rates |
|---|---|---|
| 1st. trial: | | |
| Untreated | 37.9 | |
| Bixafen [BBCH 39] | 42.6 | 125 g a.i. |
| Bixafen [BBCH 33 + 59] | 41.7 | twice 125 g a.i. |
| Bixafen + Prothioconazole [BBCH 39] | 44.9 | 75 + 150 g a.i. |
| Bixafen + Prothioconazole [BBCH 39 + 59] | 42.0 | twice 75 + 150 g a.i. |
| 2nd trial | | |
| Untreated | 30.1 | |
| Prothioconazole [BBCH 39] | 30.1 | 200 g a.i. |
| Bixafen + Prothioconazole [BBCH 39] | 39.7 | 75 + 150 g a.i./ha |

The invention claimed is:

1. A method of increasing the biomass of a plant comprising applying a biomass-increasing effective amount of bixafen to a plant in need of said increasing,
   wherein the bixafen is applied at not less than two times in the development of the plant:
   (a) the first application takes place at a time during development stages BBCH 17 to 42 of the plant, and
   (b) the second application takes place at a time during devlopment stages BBCH 43 to 70 of the plant, and
   wherein the plant is a non-transgenic plant, and is a species from the family of the true grasses (Poaceae).

2. The method of claim 1, wherein the biomass of the plant flag leaf, leaf F1, leaf F2, or a combination thereof is increased.

3. The method of claim 1, wherein the biomass of the flag leaf of the plant is increased.

4. The method of claim 1, the biomass of ears, cereal kernels, cereal kernels per ear, or a combination thereof is increased.

5. The method of claim 1, wherein said method simultaneously improves the physiological condition of the plant.

6. The method of claim 5, wherein green leaf area duration of the plant is prolonged.

7. The method of claim 5, wherein photosynthesis rate of the plant increases.

8. The method of claim 5, wherein an increased chlorophyll content, a stabilized chlorophyll content, or a combination thereof is obtained in the plant.

9. The method of claim 5, wherein delayed senescence of the plant is obtained.

10. The method of claim 5, wherein resistance and tolerance of the plant toward abiotic stress factors is increased.

11. The method of claim 1, wherein the method further comprises applying at least one active ingredient selected from the group consisting of spiroxamine, fluoxastrobin and prothioconazole.

12. The method of claim 1, wherein bixafen is applied with a dose of between 0.01 and 3 kg/ha.

13. The method of claim 1, wherein the plant is selected from the group of true grasses consisting of wheat, rye, barley, oats, millet, maize, rice, triticale, bamboo and sugarcane.

* * * * *